United States Patent [19]

Struewing

[11] Patent Number: 5,654,341
[45] Date of Patent: Aug. 5, 1997

[54] LOW PH SKIN-TREATMENT COMPOSITION

[75] Inventor: Sharon Struewing, Cincinnati, Ohio

[73] Assignee: The Andrew Jergens Company, Cincinnati, Ohio

[21] Appl. No.: 420,060

[22] Filed: Apr. 11, 1995

[51] Int. Cl.⁶ .......................... A61K 31/14; A61K 31/01
[52] U.S. Cl. .................. 514/642; 514/762; 514/789; 514/975
[58] Field of Search .................... 514/642, 762, 514/789, 975; 424/70.27, 70.28

[56] References Cited

U.S. PATENT DOCUMENTS

| | | | |
|---|---|---|---|
| Re. 29,814 | 10/1978 | Snyder | 514/772.6 |
| 3,818,105 | 6/1974 | Coopersmith et al. | 514/789 |
| 4,168,144 | 9/1979 | Curry et al. | 8/426 |
| 4,252,695 | 2/1981 | Homma et al. | 252/547 |
| 4,315,912 | 2/1982 | Kalopissis et al. | 424/70.27 |
| 4,369,250 | 1/1983 | Gindler | 435/18 |
| 4,710,314 | 12/1987 | Madrange et al. | 252/117 |
| 4,711,776 | 12/1987 | Suzuki et al. | 424/70.28 |
| 5,019,376 | 5/1991 | Uick | 424/70.28 |
| 5,143,518 | 9/1992 | Madrange et al. | 8/405 |
| 5,248,445 | 9/1993 | Rizvi et al. | 252/174.15 |

*Primary Examiner*—Kevin E. Weddington
*Attorney, Agent, or Firm*—Oblon, Spivak, McClelland, Maier & Neustadt, P.C.

[57] ABSTRACT

A low pH skin-treatment composition employs cationic surfactants generally known to be skin irritants and a fatty acid, together with a hydrocarbon component in an oil-in-water emulsion. The addition of fatty acid to the cationic surfactant appears to form a complex which prevents the cationic surfactant from irritating the skin and at the same time substantially reduces pH of the composition. The resulting composition is not skin irritating, and reflects a pH of about 2-4. The composition may be used to restore pH of skin after exposure to alkaline compositions, and as a vehicle for the administration of active agents having an acidic pH.

13 Claims, 5 Drawing Sheets

LOW PH SKIN-TREATMENT COMPOSITION

BACKGROUND OF THE INVENTION

1. Field of the Invention

This invention pertains to a composition especially adapted for treatment of mammalian skin, in particular, human skin. The composition is characterized by a low pH, and suitable for topical administration to the skin.

2. Background of the Prior Art

Mammalian skin, and human skin in particular, has a normal pH generally in the range of 4–6. A variety of agents that are commonly encountered and used for health and/or beauty care, including soaps and detergents, tend to raise skin pH above its general value. The skin acts as a general buffer zone or protectant against outside agents, and a change in the pH may hamper or limit the ability of the skin to provide its protective functions. Recovery of pH in the skin, after exposure to soaps and the like, is particularly retarded in certain classes that might be considered "at risk".

One common form of skin-treatment compositions can be characterized as oil-in-water emulsions, in which an oleaginous phase, predominantly hydrocarbon, generally present in a minor amount, is prepared in an emulsion with water or an aqueous phase. To maintain the stability of such emulsions, a surfactant is commonly employed. Nonionic and anionic surfactants are familiar to those of skill in the art. In general cationic surfactants, such as cetyltrimethylammonium bromide, although sometimes used as such as cetyltrimethylammonium bromide, although sometimes used as active agents in anti-bacterial preparations, are not conventionally used in skin treatments, due to their irritation potential. Indeed, cetyltrimethylammonium bromide (CTAB) is considered a strong irritant to the skin according to the Federal Health and Safety Association (FHSA). A rare exception to the strongly irritating nature of this class of surfactants is distearyldimmonium chloride, which has a markedly lower irritant characteristic, and is currently used in skin care products such as EVERSOFT™ (Andrew Jergens Company), CUREL™ and SOFTSENSE™ (Bausch & Lomb) and AVEENO™ (S. C. Johnson). Nonetheless, wider scale use of cationic surfactants in skin care emulsions would be desirable, for a variety of reasons. Cationic surfactants carry a positive charge. This is advantageous in light of the negatively charged characteristic of skin. Moreover, nonionic surfactants do not thicken emulsions, and require specific preservatives for use. Anionic surfactants carry a negative charge. Anionic surfactants have been demonstrated to cause damage to the stratum corneum barrier. Indeed, sodium lauryl sulfate, an anionic surfactant, is often used as a positive control in irritation tests.

Due to the high irritant character of cationic surfactants, their use in the prior art in compositions for topical application has been limited, principally, to compositions for the treatment of hair. Hair, like skin, is substantially negative, and thus substantively attractive to the cationic surfactant. Among the prior art directed to such compositions include U.S. Pat. No. 5,019,376, Uick, described as being particularly useful as hair conditioning compositions, with a pH of 2–5, and U.S. Pat. No. 4,252,695, Homma et al, with a pH of 5, and again devoted to hair conditioning. Other hair conditioning art includes U.S. Pat. No. 4,711,776, Suzuki et al, U.S. Pat. No. 5,143,518, Medrange et al, and U.S. Pat. No. 5,248,445, Rizvi et al. Hair colorants are described in U.S. Pat. No. 4,168,144, Curry et al. Medrange and Curry are directed to combinations of cationic surfactants and fatty acids which combinations exhibit basic pH values and are unsuitable for the treatment and preservation of the natural pH of human skin. None of the references identified discloses a low pH skin conditioning treatment. U.S. Pat. No. 4,710,314, Medrange et al, is also directed to a composition using cationic silicone polymers, but not the cationic surfactants of the claimed invention. This case is again directed to hair treatment compositions.

A different type of skin-conditioning composition, which is not an emulsion, is addressed in International Publication WO93/07856, Deckner et al, which is directed to a polyacrylamide gel, specifically indicated to be nonionic. The reference specifically states that surfactants are not be used, page 10, lines 28–31. The reference does establish a variety of reasons for preparing low pH skin-treatment compositions, which include, in addition to augmenting or enhancing the buffering action of skin in response to alkaline materials, using the low pH formulations as better vehicles for skin-active agents which are applied topically, such as keratolytic agents, anti-acne agents and the like. There are a variety of pharmaceuticals which exhibit low (acidic) pH values, and thus are better suited to a low pH carrier.

Fatty acids (saturated and unsaturated) constitute a class of compounds commonly used in many skin care products as opacifiers, thickeners and emulsion stabilizers. The general structure for saturated fatty acids is $C_nH_{2n}CO_2$, while unsaturated fatty acids contain at least one double bond, $C_nH_{2n-x}CO_2$. In general saturated fatty acids with more than 10 carbon atoms are solid at room temperature, and may be unsuitable for use in liquid emulsion skin care compositions. Unsaturated fatty acids are generally liquid at room temperature. Stearic acid is a widely used saturated fatty acid, generally used in the form of sodium stearate. This compound finds wide application as a soap emulsifier. In general, fatty acids appear as mixtures of other closely related acids. Commercially available stearic acid contains a mixture of $C_{18}$ and $C_{16}$ acids. Similarly, palmitic acid is a mixture of $C_{16}$ and $C_{14}$ acids.

Accordingly, it remains a goal of those of skill in the art to provide a low pH skin care composition that can be used to address or neutralize the effects of alkaline materials such as soaps and detergents which cause the skin pH to rise above normal skin pH of 4–6.

A further object of those of skill in the art is to find a method for using cationic surfactants in skin care emulsions without causing skin irritation. An additional object of the art is the provision of a skin care composition with low skin irritation, low pH and employing fatty acids as an agent therein.

SUMMARY OF THE INVENTION

The objects set forth above, and additional objects made clear by the disclosure set forth below, are achieved by the provision of a low pH skin care composition which includes a cationic surfactant, a saturated or unsaturated fatty acid, and an oleaginous phase, generally a hydrocarbon, such as mineral oil or the like. An emulsion is prepared, with the balance being substantially water, or an aqueous phase based on water.

In its broadest embodiments, the invention requires sufficient cationic surfactant to be present such that a stable emulsion is provided, and that the overall composition exhibits a pH below 4, preferably 2–4. The fatty acid component is incorporated in an amount sufficient to reduce or suppress skin irritation caused by the presence of the cationic surfactant, apparently by complexing with the cationic surfactant, forming a bulky complex with less freedom in the active agents of the cationic surfactant that irritate the skin and cause the reduction in pH. The oleaginous or hydrocarbon phase is present in amounts sufficient to provide good emollient and "feel" properties, with the balance being water. Additional compounds, including humectants, dyes, perfumes, and other components which effect the aesthetics of the emulsion prepared, making it more suitable for application to the skin, may be added in amounts that do not effect the basic low pH, low skin irritation and emulsion characteristics of the composition.

DETAILED DESCRIPTION OF THE INVENTION

The inventive skin care composition is an oil-in-water emulsion, and is therefor based on an aqueous preparation from which an emulsion is prepared. The aqueous preparation is preferably water. In addition to water, there are three required components of the inventive emulsion: (1) a cationic surfactant, (2) a fatty acid component and (3) a hydrocarbon phase, such as mineral oil. The amounts of these three essential components are not critical to the invention, provided the goals of low pH (2–4), low skin irritation and stable emulsion properties are obtained. Nonetheless, broadly stated, the cationic surfactant and fatty acid are generally present in amounts of 0.1–30 percent, by weight, based on the total composition. A preferred range is 0.1–10 percent, by weight. The hydrocarbon phase is generally present in an amount of 0.1–50 percent, by weight, based on the total composition. A preferred range is 0.5–30 percent, by weight. As the hydrocarbon phase is provided primarily as an emollient, and to provide an acceptable feel and aesthetic texture and appearance to the composition, the amount included will vary substantially with the identity of the hydrocarbon composition. In its broadest embodiment, these three components are present together with water. cationic surfactants include quaternary ammonium compounds. These may be monoalkyl, dialkyl or trialkyl, and are represented by Formulas I–III, below. Monoalkyl and dialkyl formulations are preferred from the point of view of solubility and stability.

FORMULA I

FORMULA II

FORMULA III a, b, c=Low molecular weight groups (e.g., $CH_3$, $CH_2$—$CH_3$, H)
R=Hydrophobic group (e.g., $C_8$-$C_{18}$ hydrocarbons)
X=Anionic counter ion (e.g., bromide, chloride, methylsulfate)

Suitable cationic surfactants were prepared in a simple emulsion whose composition is reflected in Table A below.

TABLE A

| INGREDIENT | A PERCENT (WEIGHT) | B PERCENT (WEIGHT) |
|---|---|---|
| Water | 77.50 | 76.50 |
| Glycerin | 10.00 | 10.00 |
| Polymer Jr | 0.20 | 0.20 |
| Ceteareth-20 | 0.80 | 0.80 |
| Cetearyl Alcohol | 2.00 | 2.00 |
| Petrolatum | 3.00 | 3.00 |
| Dimethyicone | 2.00 | 2.00 |
| Mineral Oil | 3.00 | 3.00 |
| Stearic Acid | 0.00 | 1.00 |
| Cationic Surfactant | 1.50 | 1.50 |

The pH of the emulsion was taken with and without the addition of stearic acid (1.00 percent by weight). This formulation was used to determine the pH of the various cationic surfactants at a concentration of 1.50 percent by weight.

TABLE B

| CATIONIC SURFACTANT | pH RESULTS A | pH RESULTS B |
|---|---|---|
| Cetrimonium Bromide (monoalkyl) | 4.35 | 2.66 |
| Behentrimonium Chloride (monoalkyl) | 5.45 | 3.82 |
| Distearyldimmonium Chloride (dialkyl) | 4.50 | 2.69 |
| Tricetylmonium Chloride (trialkyl) | 5.04 | 3.44 |
| Quaternium 52 (phosphate ion) | 6.48 | 4.61 |
| Methyl Bis(polyethoxy Ethanol) | 5.99 | 3.43 |
| Coco-Ammonium Chloride (dialkoxy-alkyl) | | |
| Palmitoylethyl Hydroxyethylmonium Methylsulfate (methylsulfate ion) | — | 2.94[1] |
| Dimethyl Stearyl Benzyl Ammonium Chloride (Benzyl Quat) | — | 2.40[2] |

[1]Fatty Acid = isostearic acid
[2]Stearic acid concentration = 2.5 percent

As noted, the cationic surfactant increases pH of the composition. Accordingly, the amount of the cationic surfactant must be controlled to avoid increasing pH above about 4, and similarly to avoid a skin irritation. The amount of cationic surfactant is carefully controlled in conjunction with the amount of fatty acid present. Nonetheless, a broad range of 0.1–30 percent by weight, based on the total composition, is generally suitable for the invention. A preferred range is 0.1–10 percent by weight.

Suitable fatty acids for use in this invention include most conventional fatty acids, that is, fatty acids which are liquid at room temperature. This includes relatively low molecular weight saturated fatty acid, $C_nH_{2n}CO_2$, with $n \leq 9$, and unsaturated fatty acids of the formula $C_nH_{2n-x}CO_2$. Preferred embodiments include saturated fatty acids of 12–20 carbon atoms. Stearic, palmitic, oleic, linoleic and linolenic acids (linoleic and linolenic including two and three double bonds, respectively).

The fatty acid component is incorporated in an amount sufficient to reduce the pH of the composition to a value of 2–4. As set forth below, the addition of the fatty acid dramatically drops pH at relatively low concentrations. At the same time, the fatty acid apparently complexes with the cationic surfactant, to provide a bulky complex which reduces or suppresses skin irritation. Without being bound by the explanation, it is believed that the complexes are formed by ion pairing of the cation of the surfactant with the carboxylate anion of fatty acid. As a result of the pairing, HX is released, which lowers the pH of the emulsion. Although no cosmetic formulations are described, this theory is supported by the discussion in *Cosmetics: Science and Technology*, Volume 1 (Balsm et al, Editors, 2d Edition). Thus, the fatty acid component is incorporated in amounts of about 0.1–30 percent by weight. More preferably, the fatty acid is present in amounts of 0.1–10.0 percent by weight, again based on the weight of the composition.

The oleaginous or hydrocarbon phase is selected from any of a variety of well-known oil or emollient components. The principal criteria is that the emollient must be stable in a low pH environment. Representative oil components include hydrocarbon oils, (e.g., petrolatum, mineral oil, polydecene), silicone oils, (both volatile and non-volatile), fatty alcohols, (e.g., cetyl, isostearyl, guerbet), waxes (e.g., hydrocarbon waxes, meadowfoam seed oil) and fatty acid esters (e.g., isopropyl myristate, myristyl myristate). The hydrocarbon phase is advantageously used in an amount sufficient to give the composition an acceptable feel and skin conditioning effect, generally in an amount of 0.5–30 percent by weight, based on the total weight of the composition.

In addition to water, the aqueous phase, which constitutes the balance of the composition, can include humectants, such as glycerin, propyleneglycol or sorbitol, generally in an amount of 0–40 percent by weight, based on the total weight of the composition. Other water soluble materials may be added including keratolytic agents, water soluble polymers (e.g., polymer JR), preservatives, moisturizing agents such as amino acids, colorings and fragrances. These additives are generally incorporated in an amount of no more than 5 percent by weight. Pharmaceutical agents, if incorporated, are incorporated in an amount effective to achieve the pharmaceutical goal, but generally, in no more than 5 percent by weight. Water is generally in the range of 50–95 percent by weight.

EXAMPLES

The invention addressed herein is exemplified in the working and comparative examples set forth below. These examples are not intended to limit the invention in any way.

pH Reduction by Addition of Fatty Acid

Figure 1:
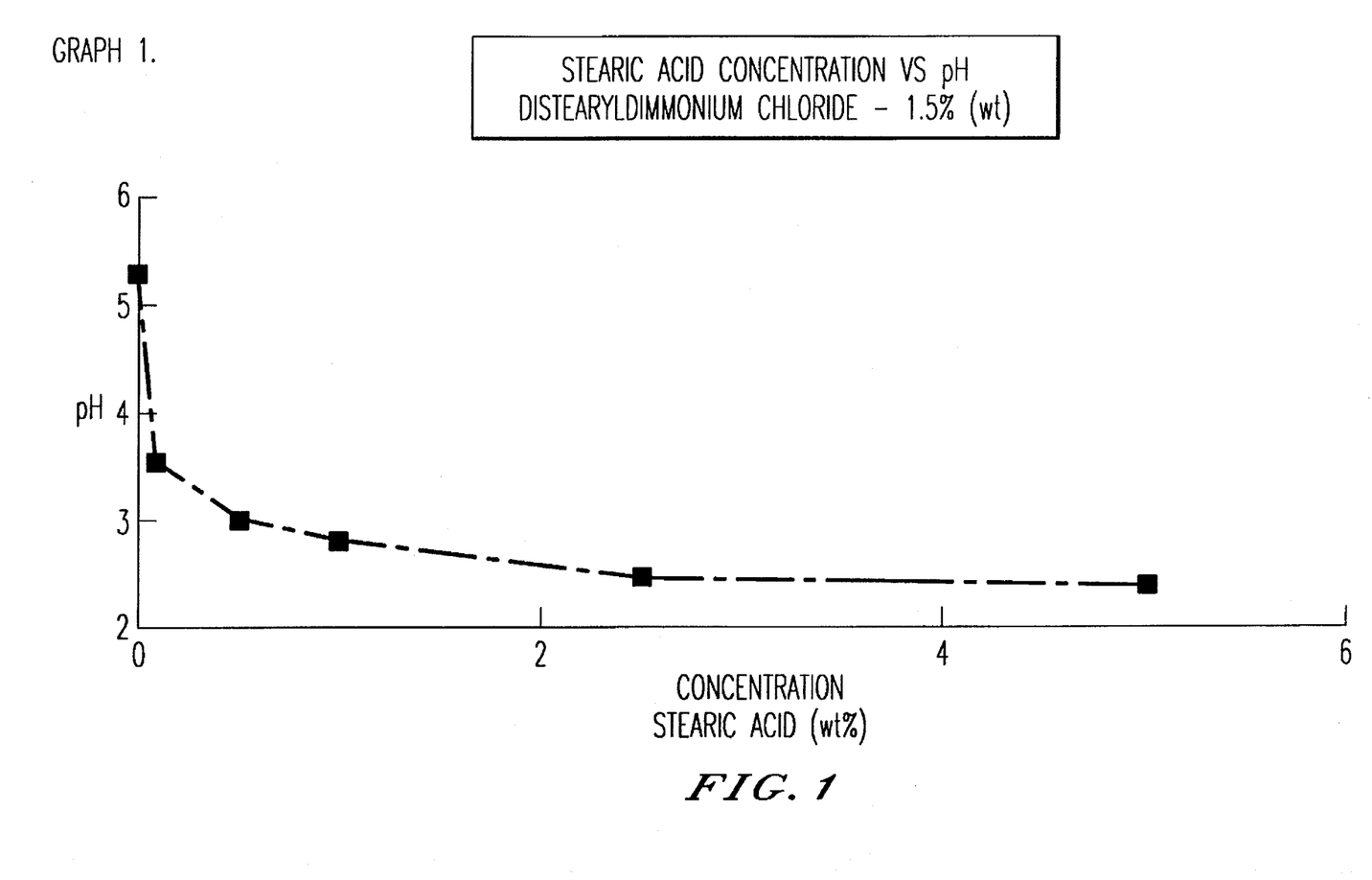
FIG. 1 (graph 1) is a graphic demonstration of the effect of stearic acid concentration on pH of a solution bearing a cationic surfactant (distearyldimmonium chloride).

A cationic surfactant-based emulsion, according to the formula set forth in Table A above, was prepared, using distearyldimmonium chloride as the cationic surfactant at a 1.5 percent weight concentration. As an exemplary fatty acid, stearic acid was selected and added to the described emulsions. The result is reflected in FIG. 1. As shown therein, dramatic reductions in pH are reflected by the addition of relatively low amounts of stearic acid, an amount of about 0.1 percent being sufficient to drop the pH from a starting point above 5 to a value within the intended scope of the invention, that is, between 2 and 4. This sharp drop in pH upon the addition of fatty acid tends to confirm the theory advanced above, that the fatty acid and cationic surfactant form a bulky complex which liberates HX, resulting in a sharp drop in pH. Even upon the addition of substantial amounts of fatty acid, the pH remains above 2, again clearly indicating that the addition of the fatty acid alone is not responsible for the pH drop.

Figure 2:
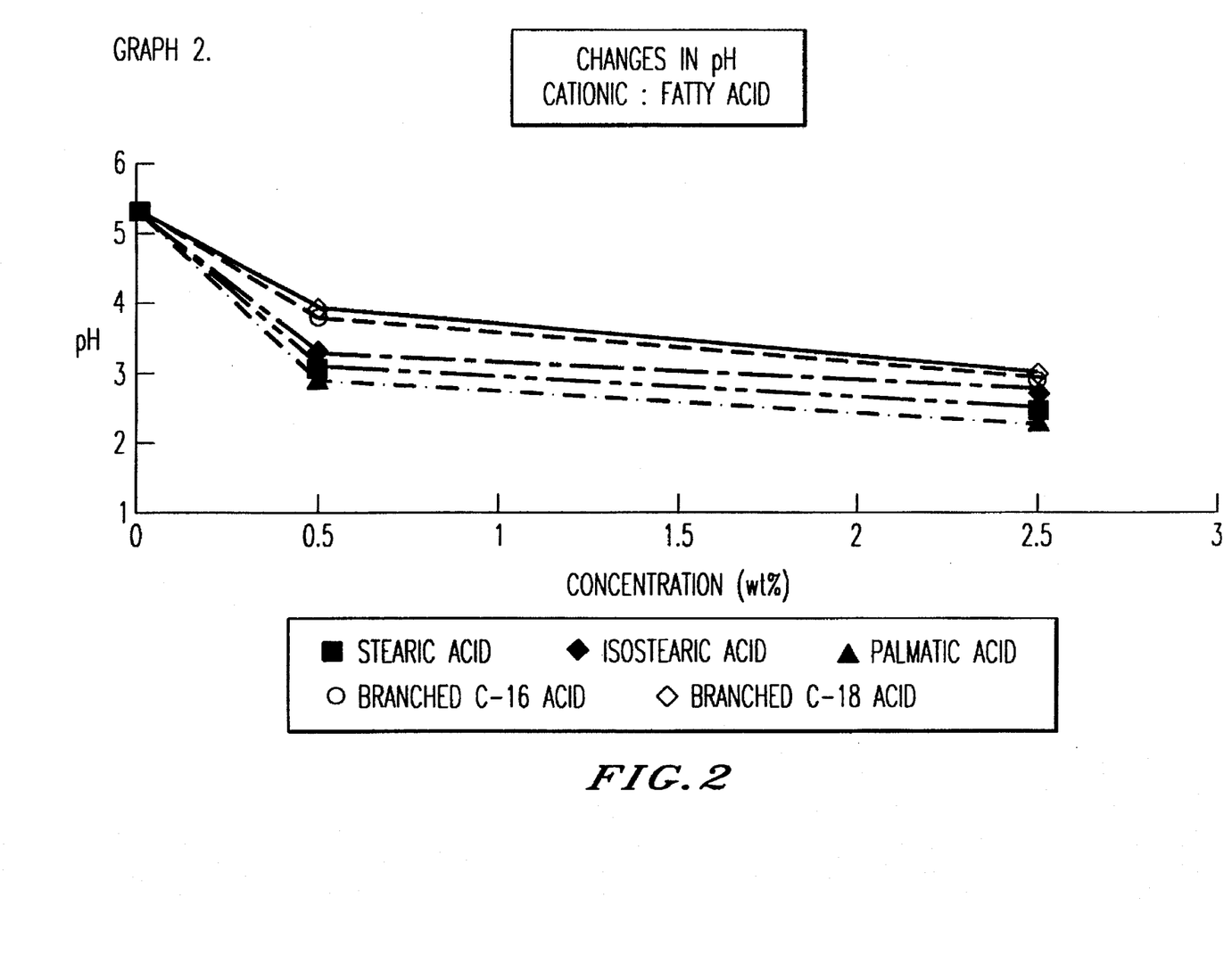
FIG. 2 (graph 2) graphically compares the changes in pH caused by the addition of various fatty acids to a cationic surfactant-containing composition.

The above-described experiment was also conducted with other representative fatty acids. The results are depicted in FIG. 2. As shown in FIG. 2, the addition of all fatty acids selected resulted in a drop of pH on the addition of at least 0.5 weight percent to a value below 4. Bulkier branched fatty acids did not cause the extreme drop in pH upon the addition of minor amounts that was observed in connection with straight-chain fatty acids. Accordingly, the fatty acid may be selected so as to tailor the resulting desired pH within the identified range of the invention.

Figure 3:
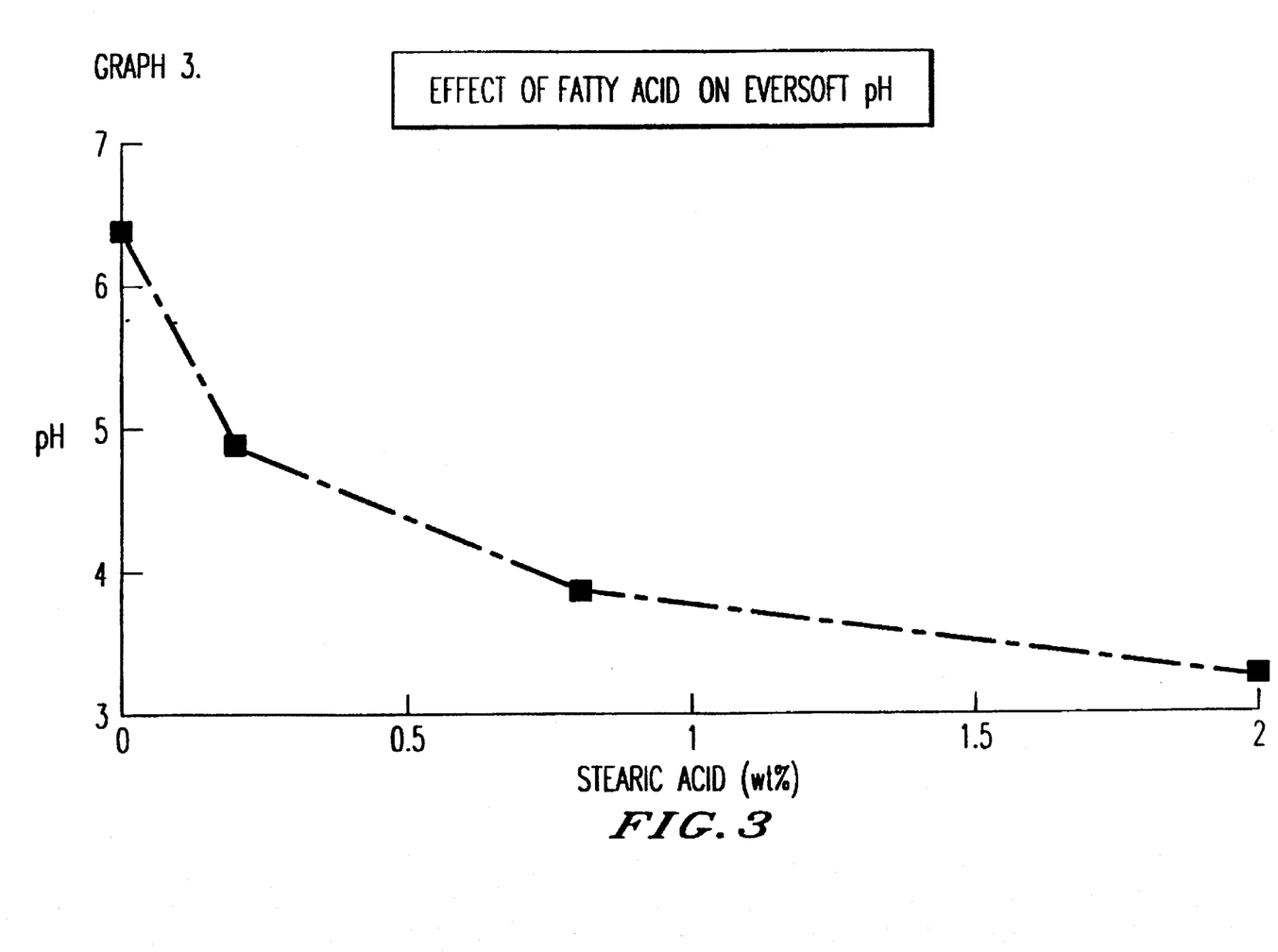
FIG. 3 (graph 3) is a graphic representation of the change in pH caused by the addition of fatty acid (stearic acid) to a commercial skin treatment product, EVERSOFT™.

As noted previously, certain commercial skin compositions are available which include the cationic surfactant distearyldimmonium chloride. A representative fatty acid, stearic acid, was added to the EVERSOFT™ preparation and pH measured, with the results reflected in FIG. 3. Clearly, even in commercial preparations designed for skin care with pH above 4, modification within the scope of the invention disclosed and claimed herein results in a dramatic drop in pH, such that the skin care composition may be modified so as to improve the buffering action of the skin by returning it to its normal pH after exposure to alkaline materials.

Skin Irritation Tests

As noted above, a principal difficulty in employing cationic surfactants in skin treatment compositions is the widely held belief that such compositions are skin irritants. A test was conducted to measure the skin irritation potential of the low pH formulations of the invention. The protocol included Occlusive 25 mm Hilltop Chambers on the volar forearms. The study was a three-day study with patches applied each day. The sites tested were evaluated by the Transepidermal Water Loss Measurements methodology, Simion et al, 1991. Transepidermal water loss was assessed prior to the first patch and three hours after the last patch. TEWL measures the rate at which water passes from the skin into the environment (Van der Valk et al, 1984). Thus, skin sites with high TEWL rates in the study indicate damage to the stratum corneum barrier. The cationic surfactants tested included cetyltrimethylammonium bromide (CTAB) and distearyldimmonium chloride (DSDC). The formulations employed in the skin irritation study are reflected in Table 1. The formulations also contained methyl and propyl paraben, as well as DMDM Hydantoin or Quaternium-15 as preservatives. Quaternium-15 was used in Formula G because this was a previously tested formula. Formulas A and B are without and with fatty acid, respectively. Formula C contains a pH adjustor, lactic acid, to study the low pH effect. Formulas D and E are monoalkyl cationic surfactants with and without fatty acid, respectively. Formula F has a base pH adjustor, sodium hydroxide, to bring the pH close to neutral. Formula G is a monoalkyl cationic formula previously found to be irritating. Results from the irritation study are given in Table II. TEWL values are reported as degree of change from day 3–day 1.

TABLE I

|  | A | B | C | D | E | F |
| --- | --- | --- | --- | --- | --- | --- |
| Water | 66.60 | 66.50 | 65.46 | 66.60 | 66.60 | 62.60 |
| Glycerin | 10.00 | 10.00 | 10.00 | 10.00 | 10.00 | 10.00 |
| Polymer JR | 0.20 | 0.20 | 0.20 | 0.20 | 0.20 | 0.20 |
| DSDC | 1.50 | 1.50 | 1.50 | — | — | — |
| CTAB | — | — | — | 1.50 | 1.50 | 1.50 |
| Stearic Acid | — | 1.00 | — | — | 1.00 | 1.00 |
| Cetearyl Alcohol | 2.00 | 2.00 | 2.00 | 2.00 | 2.00 | 2.00 |
| Mineral Oil | 3.00 | 3.00 | 3.00 | 3.00 | 3.00 | 3.00 |
| Dimethicone | 2.00 | 2.00 | 2.00 | 2.00 | 2.00 | 2.00 |
| Petrolatum | 3.00 | 3.00 | 3.00 | 3.00 | 3.00 | 3.00 |
| Preservatives | 0.70 | 0.70 | 0.70 | 0.70 | 0.70 | 0.70 |
| Lactic Acid, 88% | — | — | 1.14 | — | — | — |
| NaOH 5% (wt) Solution | — | — | — | — | — | 3.00 |
| Hydroxyethyl Cellulose | — | — | — | — | — | — |
| pH | 4.50 | 2.69 | 2.15 | 4.34 | 2.66 | 7.53 |

TABLE II

|  | A | B | C | D | E | F |
| --- | --- | --- | --- | --- | --- | --- |
| TEWL DAY 3-DAY 1 | 0.70 ± 0.50 | 0.37 ± 0.49 | 1.02 ± 0.36 | 6.23 ± 1.57 | 2.03 ± 0.61 | 3.74 ± 0.90 |

The results clearly indicate that the addition of the fatty acid lowers the irritation observed. This is especially evident in Formula D, which contains a monoalkyl surfactant, and is irritating, but, upon the addition of stearic acid, Formula E, the irritation is lowered dramatically. All of the reduced pH formulas were non-irritating. Formula C, pH 2.15, containing lactic acid, did result in higher TEWL values than the other low pH formulations containing stearic acid, demonstrating greater damage to the stratum corneum barrier. The neutral adjusted fatty acid formula, Formula F, exhibited irritation. The irritation is probably caused by the strong attraction of sodium hydroxide to the stearic acid to form sodium stearate. This attraction keeps the fatty acid from complexing with the cationic surfactant, so the monoalkyl quaternary compound is not completely shielded by the stearic acid carboxylate anion. Sodium lauryl sulfate, SLS, 0.5 percent by weight, was used as the positive control. The SLS sites exhibited the most severe irritation with a TEWL value of 46.80±8.90.

Skin pH Studies

Skin surface pH studies were also conducted to study the effects of the low pH formulations of the invention on skin pH. Measurements were made on the volar forearm before and after application of the test product. Skin surface pH was generated using a flat-surface electrode, calibrated in standard buffer solutions at pH 4.0 and pH 7.0. The electrode was dipped in deionized water before each measurement.

Using a five-person panel, four formulations were tested for effect on the skin surface pH of the forearm. The formulas tested are listed in Table III. Formulas H and I are cationic lotions with various levels of cationic surfactant and fatty acid. Formulas J and K are nonionic emulsions. Formula J represents a general lotion, while Formula K contains a lactic acid buffer system to observe pH effects. The results are reflected in FIG. 4.

TABLE III

|  | H | I | J | K |
| --- | --- | --- | --- | --- |
| Water | 75.50 | 68.00 | 76.00 | — |
| Glycerin | 10.00 | 10.00 | 10.00 | 10.00 |
| Cetearyl Alcohol | 2.00 | 2.00 | 2.00 | 2.00 |
| Stearic Acid | 1.00 | 5.00 | — | — |
| DSDC | 1.50 | 5.00 | — | — |
| Mineral Oil | 10.00 | 10.00 | 10.00 | 10.00 |
| Ceteareth-20 | — | — | 2.00 | 2.00 |
| Lactic Acid Buffer | — | — | — | 76.00 |
| pH | 2.72 | 2.19 | 5.18 | 4.19 |

Figure 4:
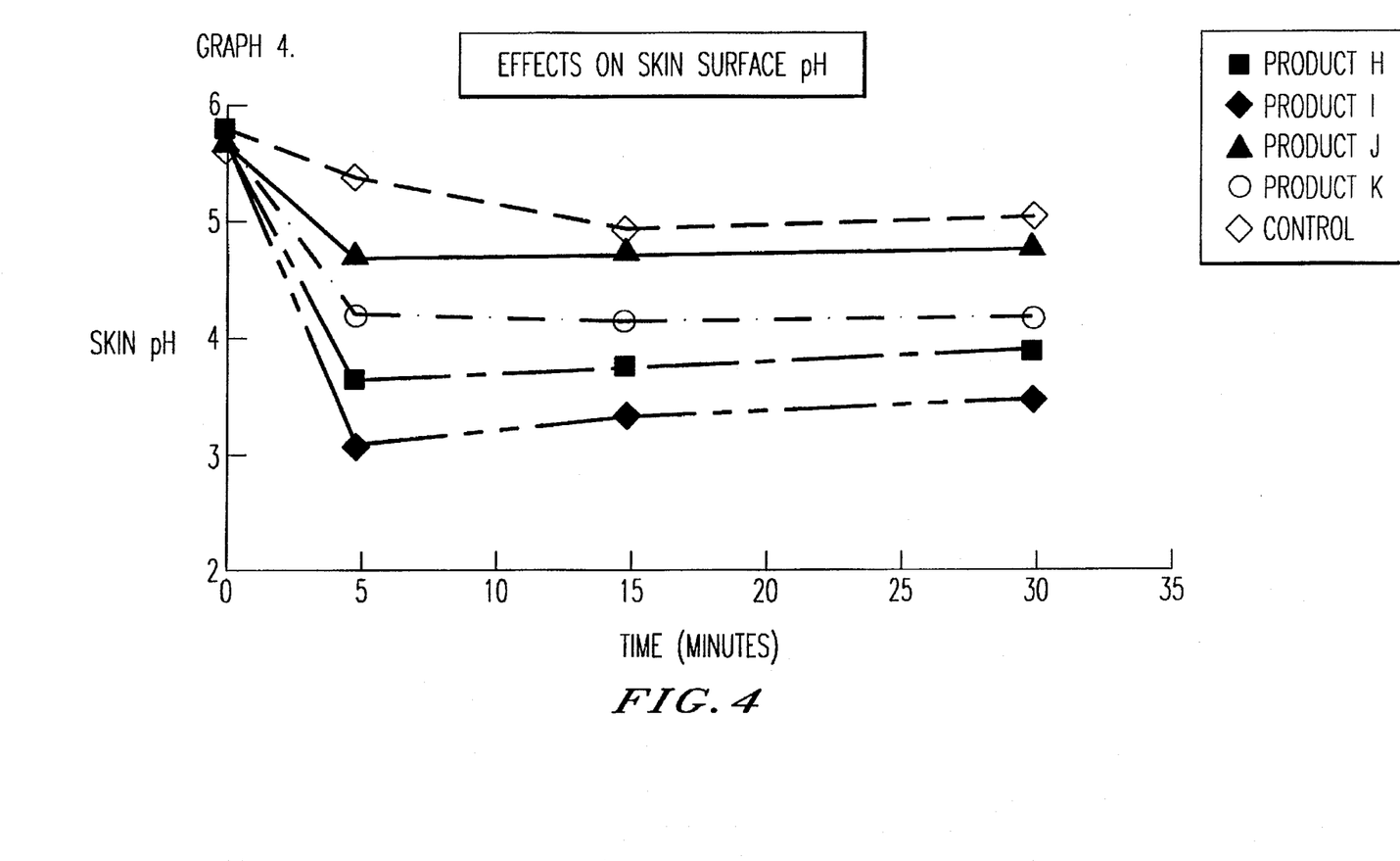
FIG. 4 (graph 4) is a graphic representation on the effects of the application of inventive and non-inventive products on pH measured at the skin surface of test subjects.

Clearly, the cationic formulations, Products H and I, had the greatest effect in lowering skin surface pH. Application of Product I, with higher levels of cationic surfactant and fatty acid components resulted in the lowest skin surface pH.

The same study was repeated, however, this time the formulations were applied immediately after washing with soap, rather than application to untreated skin. Volar forearms were washed for twenty second with a commercial soap product, 1 percent solution pH=10.7, followed by a fifteen second rinse of water. Measurements were made before and after soap washing. The formulations were applied five minutes after rinsing to allow time for the pH to be measured between washing and application of the test composition. The results are reflected in FIG. 5.

Figure 5:
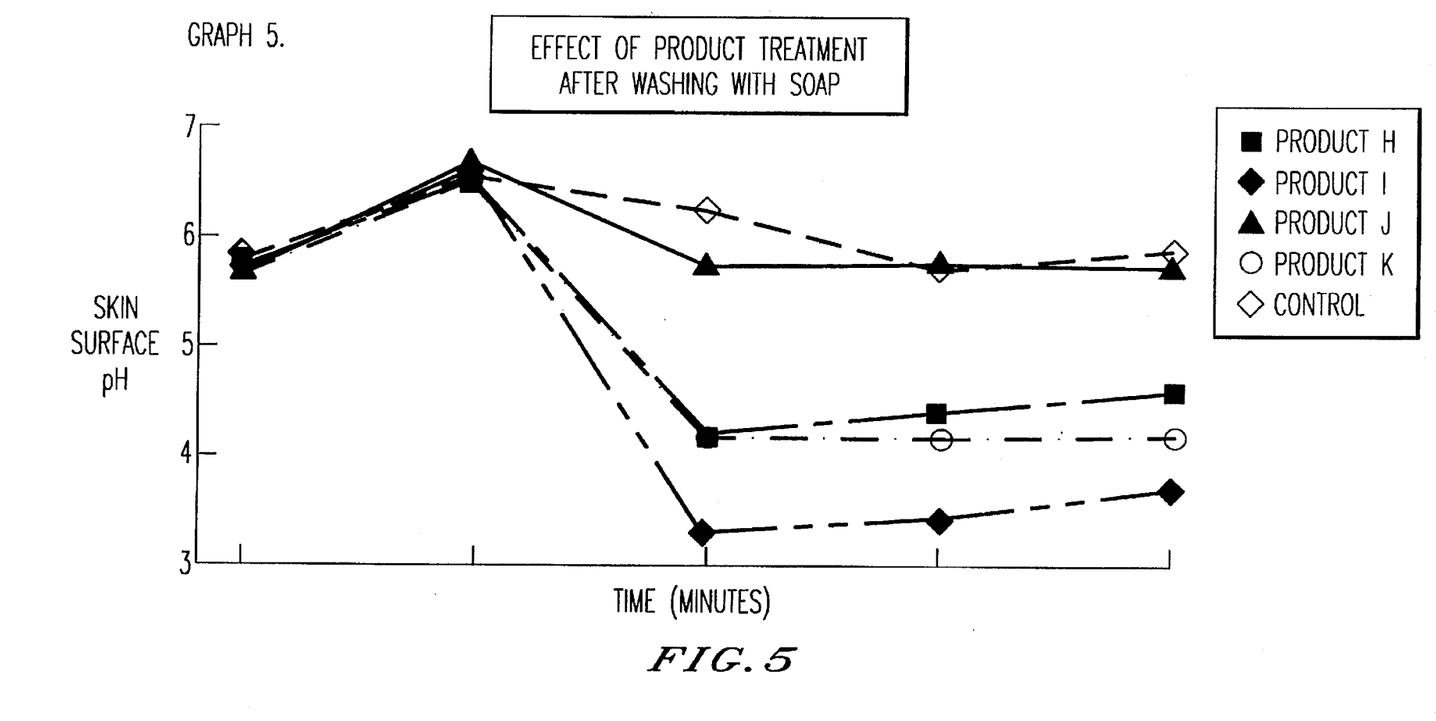
FIG. 5 (graph 5) is a graphic representation of the effect of treatment of the skin with the products reflected in FIG. 4 on skin surface pH after washing the skin with soap.

Skin surface pH was elevated to 6.5–6.9 after washing with soap followed by rinsing. The sites treated with the nonionic formulation, Product J, and the control (no product application) gave the same pH. After thirty minutes, the pH values were slightly above the initial pH values (prior to washing). The low pH formulations of the claimed invention (H and I) resulted in a substantial reduction in skin pH.

Accordingly, it is clear that the claimed invention provides a skin care preparation which permits the use of cationic surfactants, whose prior use has been limited by reason of their irritating properties. The addition of a fatty acid results in a low pH emulsion which is non-irritating to the skin. This is particularly surprising when it is noted that the pH of the formulations of the claimed invention are typically below 3. Generally, such compositions would be considered to be irritating to the skin, but when tested were found non-irritating using patch testing. Skin surface testing, both with and without soap-induced high pH values, show marked decrease in pH values upon application of the claimed invention.

This invention has been disclosed in terms of a generic description, specific embodiment, and by example. The embodiments and examples are not intended to be limiting, and variations will occur to those of ordinary skill in the art, without the exercise of inventive faculty. In particular, other identities for cationic surfactants, fatty acids, and the oleaginous phase beyond those specifically recited are well known to those of skill in the art for use, separately, in skin care formulations, and may be used herein without departing from the scope of the invention. Similarly, weight percentages, additions of stabilizing and/or aesthetic components and the like remain within the scope of the invention. These and related variations remain within the scope of the invention, save as excluded by recitation of the claims set forth below.

What is claimed is:

1. A low pH skin-treatment composition, which comprises the following components:
   (a) a cationic surfactant;
   (b) a fatty acid;
   (c) an oleaginous hydrocarbon comprising at least one member selected from the group consisting of hydrocarbon oils, hydrocarbon waxes, silicon oils, non-hydrocarbon waxes, fatty acid esters and mixtures thereof; and
   (d) water, said cationic surfactant, fatty acid and hydrocarbon components being present in amounts sufficient to provide a non-skin irritating emulsion with pH of about 2–4, with water constituting the balance of said composition.

2. The composition of claim 1, wherein said cationic surfactant component is present in amounts of 0.1–30 percent by weight, based on the weight of the composition, said fatty acid is present in amounts of 0.1–30 percent by weight based on the weight of the composition and said hydrocarbon component is present in amounts of 0.1–50 percent by weight based on the weight of the composition.

3. The composition of claim 1, wherein said cationic surfactant comprises a monoalkyl or dialkyl quaternary ammonium compound.

4. The composition of claim 3, wherein said cationic surfactant is selected from the group consisting of cetrimonium bromide, behentrimonium chloride, distearyldimmonium chloride, tricetylmonium chloride, Quaternium 52, methyl bis(polyethoxyethanol) coco-ammonium chloride, palmitoylethyl hydroxyethylmonium methylsulfate, dimethyl stearyl benzyl ammonium chloride and mixtures thereof.

5. The composition of claim 1, wherein said fatty acid is a saturated fatty acid of the formula $C_nH_2CO_2$ with $n \leq 9$ and unsaturated fatty acids of the formula $C_nH_{2n-x}CO_2$ with $n \leq 21$ and x an even integer from 2–6.

6. The composition of claim 5, wherein said fatty acid is selected from the group consisting of stearic, palmitic, oleic, linoleic, linolenic acids and mixtures thereof.

7. The composition of claim 1, wherein said cationic surfactant component comprises at least one of distearyldimmonium chloride and cetyltrimethylammonium bromide and said fatty acid component comprises stearic acid.

8. The composition of claim 1, wherein said composition further comprises at least one of a humectant, keratolytic agent, water-soluble polymer, preservative, moisturizing agent, coloring, and a fragrance.

9. The composition of claim 8, wherein said humectants are present in an amount of 0–10 percent by weight, based on the total weight of the composition, and said keratolytic agent, water-soluble polymer, preservative, moisturizing agent, coloring or, fragrance are each present in an amount of 0–5 percent by weight, based on the total weight of the composition.

10. A method of softening skin, comprising applying the composition of claim 1 to said skin in an amount sufficient to provide emollient properties, without skin irritation.

11. A method of reducing skin pH from a value above 4, by applying the composition of claim 1 thereto, in an amount sufficient to reduce the pH of said skin.

12. A method of returning skin pH to a value of 4–6 subsequent to exposure to alkaline materials which raise the pH of said skin to a value above 6 upon exposure to said skin, comprising applying the composition of claim 1 to said skin in an amount sufficient to reduce the pH of said skin to a value between 4 and 6.

13. A method of administering keratolytic agents having an acidic pH to skin of a patient by topical administration comprising admixing said pharmaceutical agent with the composition of claim 1, and applying the resulting admixture to said skin of said patient in an amount sufficient to provide a keratolytically effective amount of said agent.

* * * * *